(12) United States Patent
Lassen et al.

(10) Patent No.: US 11,845,716 B2
(45) Date of Patent: Dec. 19, 2023

(54) PROCESSES FOR REMOVING CARBON DISULFIDE FROM SYMMETRICAL AND ASYMMETRICAL SULFIDE PRODUCT STREAMS

(71) Applicant: Chevron Phillips Chemical Company LP, The Woodlands, TX (US)

(72) Inventors: Kenneth M. Lassen, Bartlesville, OK (US); Michael S. Matson, Bartlesville, OK (US); Daniel M. Hasenberg, Kingwood, TX (US); Dave C. Schwierman, Stinnett, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 621 days.

(21) Appl. No.: 16/904,681

(22) Filed: Jun. 18, 2020

(65) Prior Publication Data

US 2020/0339506 A1 Oct. 29, 2020

Related U.S. Application Data

(62) Division of application No. 16/396,820, filed on Apr. 29, 2019, now Pat. No. 10,774,040.

(51) Int. Cl.
*B01J 8/02* (2006.01)
*C07C 319/06* (2006.01)
(Continued)

(52) U.S. Cl.
CPC .......... *C07C 319/28* (2013.01); *C07C 319/06* (2013.01); *C07C 319/14* (2013.01);
(Continued)

(58) Field of Classification Search
CPC ... C07C 319/28; C07C 319/06; C07C 319/14; C07C 321/14; C07C 321/22;
(Continued)

(56) References Cited

U.S. PATENT DOCUMENTS 1,783,901 A 12/1930 Bottoms
2,822,400 A * 2/1958 Cinque .................. C07C 321/00
568/71

(Continued)

FOREIGN PATENT DOCUMENTS

CA 2889745 A1 * 5/2014 ............... B01J 29/89
DE 3922904 A * 1/1991 ........... B01D 53/485
(Continued)

OTHER PUBLICATIONS

Machine translation of DE-3922904 A1 (Year: 2023).*
(Continued)

*Primary Examiner* — Huy Tram Nguyen
(74) *Attorney, Agent, or Firm* — Merchant & Gould P.C.

(57) ABSTRACT

Processes for removing carbon disulfide from product streams containing a sulfide compound are performed by contacting the product stream with an alkanolamine and converting the carbon disulfide to a higher boiling point product, thereby reducing or eliminating carbon disulfide from the product stream. Subsequent removal of the higher boiling point product via distillation can lead to a purified sulfide stream with high purity.

20 Claims, 1 Drawing Sheet

(51) Int. Cl.
*C07C 319/28* (2006.01)
*C07C 319/14* (2006.01)
*B01D 3/00* (2006.01)
*B01D 3/02* (2006.01)
*C07D 263/16* (2006.01)
*C07D 263/22* (2006.01)
*C07D 277/04* (2006.01)

(52) U.S. Cl.
CPC ............... *B01D 3/009* (2013.01); *B01D 3/02* (2013.01); *B01J 8/02* (2013.01); *C07D 263/16* (2013.01); *C07D 263/22* (2013.01); *C07D 277/04* (2013.01)

(58) Field of Classification Search
CPC ........ C07C 323/25; B01D 3/009; B01D 3/02; B01J 8/02; C07D 263/16; C07D 263/22; C07D 277/04
USPC .......................................................... 422/610
See application file for complete search history.

(56) References Cited

U.S. PATENT DOCUMENTS

| | | | |
|---|---|---|---|
| 4,401,838 | A | 8/1983 | Balogh |
| 4,412,913 | A | 11/1983 | Moote |
| 6,531,103 | B1 | 3/2003 | Hakka |
| 10,159,930 | B2 | 12/2018 | Laroche |
| 10,774,040 | B1 | 9/2020 | Lassen et al. |
| 2003/0205134 | A1 | 11/2003 | Hasenberg |
| 2007/0017291 | A1 | 1/2007 | Cypes et al. |
| 2013/0267739 | A1 | 10/2013 | Fremy |
| 2016/0207854 | A1 | 7/2016 | Weissheimer |
| 2018/0221811 | A1 | 8/2018 | Vorberg et al. |

FOREIGN PATENT DOCUMENTS

| | | |
|---|---|---|
| DE | 3922904 A1 | 1/1991 |
| GB | 572690 A | 10/1945 |
| GB | 617969 A | 2/1949 |
| JP | 2005281602 A | 10/2005 |
| WO | 2009120419 A1 | 10/2009 |
| WO | 2010007006 A1 | 1/2010 |
| WO | 2018221811 A1 | 12/2018 |
| WO | WO 2020/223035 | 11/2020 |

OTHER PUBLICATIONS

International Search Report and the Written Option of the International Searching Authority in PCT/US2020/0208641 dated May 10, 2019, 9 pages.

Rich et al. "Carbon Disulfide (CS2) Mechanisms in Formation of Atmospheric Carbon Dioxide (CO2) Formation from Unconventional Shale Gas Extraction and Processing Operations and Global Climate Change." Environmental Health Insights, 2015:9(S1). pp. 35-39.

* cited by examiner

PROCESSES FOR REMOVING CARBON DISULFIDE FROM SYMMETRICAL AND ASYMMETRICAL SULFIDE PRODUCT STREAMS

This application is a divisional application of co-pending U.S. patent application Ser. No. 16/396,820, filed on Apr. 29, 2019, now U.S. Pat. No. 10,774,040, the disclosure of which is incorporated herein by reference in its entirety.

FIELD OF THE INVENTION

Sulfide compounds have wide industrial application, for instance as gas odorants, and in paper production from wood products. Impurities commonly present in sulfide product streams can result in unwanted reactivity during their intended use, as well as cause corrosion in the related machinery and equipment. The present disclosure generally relates to the removal of impurities such as carbon disulfide ($CS_2$) from product streams containing sulfide compounds.

BACKGROUND OF THE INVENTION

Product streams containing sulfide compounds also can contain impurities that are difficult to remove from the product streams directly. Impurities that have similar physical or chemical attributes to those of other components in the product stream, including the sulfide compound itself, can be particularly difficult to separate. Moreover, removal of impurities beyond a certain degree may require conditions that can be commercially impractical for large-scale production operations. Thus, it would be beneficial to develop processes that can improve the efficiency and effectiveness of removing impurities from product streams containing sulfide compounds. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The invention disclosed herein generally relates to processes for purifying a product stream containing a sulfide compound and $CS_2$. The processes can comprise (i) contacting the product stream with an alkanolamine to convert at least a portion of the $CS_2$ to a higher boiling point product, and (ii) removing at least a portion of the higher boiling point product from the product stream to form a purified sulfide stream. These processes can be applied to product streams containing a sulfide compound having formula (I):

$$R^1\text{—}S\text{—}R^2 \qquad (I).$$

Generally, $R^1$ and $R^2$ independently can be a $C_1$ to $C_{18}$ substituted or unsubstituted, cycloalkyl group or linear or branched alkyl group. In certain aspects, the sulfide compound can be dimethyl sulfide or methyl ethyl sulfide.

Various alkanolamines can be used in the disclosed processes, such as β-hydroxy amines. In some aspects, the alkanolamine can have a heteroatom-containing linking group between the hydroxy and amine groups.

Processes disclosed herein can form purified sulfide streams having low levels of carbon disulfide. For instance, the processes disclosed herein can have a ratio of the concentration of $CS_2$ present in the product stream prior to step (i) to the concentration of $CS_2$ present in the purified sulfide stream of at least about 100:1—thus, a 100-fold reduction in the $CS_2$ concentration.

Optionally, the processes disclosed herein can further comprise the steps of determining a concentration of the $CS_2$ in the product stream, and adjusting an amount of the alkanolamine contacted with the product stream based on the concentration of the $CS_2$ in the product stream. Similarly, the processes disclosed herein can further comprise the steps of determining a concentration of the $CS_2$ in the purified sulfide stream, and adjusting an amount of the alkanolamine contacted with the product stream based on the concentration of the $CS_2$ in the purified sulfide stream.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

Figure 1:
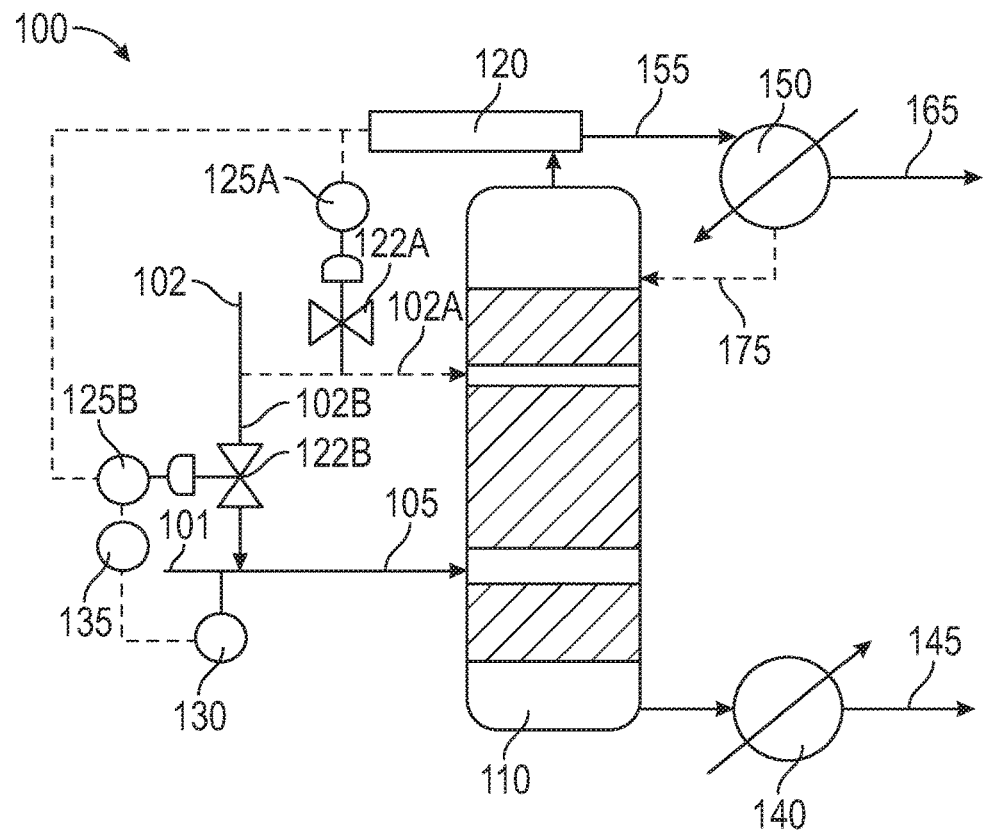
FIG. 1 illustrates a carbon disulfide removal system consistent with an aspect of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

While compositions and processes are described in terms of "comprising" various components or steps, the compositions and methods also can "consist essentially of" or "consist of" the various components or steps, unless specifically stated otherwise.

The terms "a," "an," and "the" are intended to include plural alternatives, e.g., at least one, unless otherwise specified. For instance, the disclosure of "a higher boiling point product" and "an alkanolamine" is meant to encompass one, or mixtures or combinations of more than one, higher boiling point product and alkanolamine, respectively, unless otherwise specified.

All "ppm" quantities disclosed herein refer to ppm by weight, unless specifically stated otherwise.

For any particular compound or group disclosed herein, any name or structure presented is intended to encompass all conformational isomers, regioisomers, and stereoisomers that can arise from a particular set of substituents, unless otherwise specified. For example, a general reference to pentane includes n-pentane, 2-methyl-butane, and 2,2-dimethylpropane, and a general reference to a butyl group includes an n-butyl group, a sec-butyl group, an iso-butyl group, and a t-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

The term "substituted" when used to describe a group, for example, when referring to a substituted analog of a particular group, is intended to describe any non-hydrogen moiety that formally replaces a hydrogen in that group and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

As used herein, the term "alkanolamine" refers to a compound having both a hydroxy group and an amine group. The amine group can be a primary, secondary, or tertiary amine group. Alkanolamine encompasses monoalkanolamines (one hydroxy group), dialkanolamines (two hydroxy groups), and trialkanolamines (three hydroxy groups). Additionally, the alkanolamine can contain, in some aspects, a heteroatom-containing linking group between the amine and hydroxy group(s). The alkanolamine can be linear or branched, and substituted or unsubstituted, as would be recognized by a skilled artisan.

The terms "contacting" and "combining" are used herein to describe methods and processes in which the materials or components are contacted or combined together in any order, in any manner, and for any length of time, unless otherwise specified. For example, the materials or components can be blended, mixed, slurried, dissolved, reacted, treated, compounded, impregnated, or otherwise contacted or combined in some other manner or by any suitable method or technique.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{12}$ hydrocarbyl group, or in alternative language, a hydrocarbyl group having from 1 to 12 carbon atoms, as used herein, refers to a moiety that can have 1, 2, 3, 4, 5, 6, 7, 8, 9, 10, 11, or 12 carbon atoms, as well as any range between these two numbers (for example, a $C_2$ to $C_6$ hydrocarbyl group), and also including any combination of ranges between these two numbers (for example, a $C_2$ to $C_4$ and a $C_8$ to $C_{12}$ hydrocarbyl group).

Similarly, another representative example follows for the molar ratio of alkanolamine:$CS_2$ employed in aspects of step (i) of the disclosed processes. By a disclosure that the molar ratio of alkanolamine:$CS_2$ can be in a range from about 1:1 to about 6:1, the intent is to recite that the ratio of alkanolamine:$CS_2$ can be any ratio in the range and, for example, can be equal to about 1:1, about 1.5:1, about 2:1, about 3:1, about 4:1, about 5:1, or about 6:1. Additionally, the ratio of alkanolamine:$CS_2$ can be within any range from about 1:1 to about 6:1 (for example, from about 2:1 to about 6:1), and this also includes any combination of ranges between about 1:1 and about 6:1 (for example, the alkanolamine:$CS_2$ ratio can be in a range from about 3:1 to about 4:1, or from about 5:1 to about 6:1). Further, in all instances, where "about" a particular value is disclosed, then that value itself is disclosed. Thus, the disclosure that the ratio of alkanolamine:$CS_2$ can be from about 1:1 to about 6:1 also discloses a ratio from 1:1 to 6:1 (for example, from 2:1 to 6:1), and this also includes any combination of ranges between 1:1 and 6:1 (for example, the alkanolamine:$CS_2$ ratio can be in a range from 3:1 to 4:1, or from 5:1 to 6:1). Likewise, all other ranges disclosed herein should be interpreted in a manner similar to these examples.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Many product streams containing sulfide compounds also contain impurities that are both difficult to remove and limit the ability of the sulfide product stream to be used in a variety of desirable end-use applications. For instance, dimethyl sulfide product streams often contain 2000-4000 ppm by weight of carbon disulfide ($CS_2$). While the purity of the dimethyl sulfide in the product stream is very high (e.g., greater than 98 wt. %, and often greater than 99 wt. %), ppm amounts of carbon disulfide present in the dimethyl sulfide product stream can prevent it from being used in end-use applications that require substantially "pure" dimethyl sulfide, generally requiring ppm amounts of carbon disulfide of less than 100 ppm, and in some cases, less than 20 ppm. For example, a dimethyl sulfide product with less than 1 ppm $CS_2$ may be preferred for use in ethylene plants and as a reagent for synthesizing dimethyl sulfoxide (DMSO). However, removal of carbon disulfide ($CS_2$) from dimethyl sulfide using conventional separations techniques, such as distillation, cannot approach the very low ppm levels of carbon disulfide needed to produce substantially pure dimethyl sulfide. Thus, alternative means for eliminating difficult-to-remove impurities from such sulfide product streams are needed.

Accordingly, disclosed herein are alternative processes for purifying product streams comprising (or consisting essentially of, or consisting of) a sulfide compound and carbon disulfide ($CS_2$). Such processes can comprise (or consist essentially of, or consist of) (i) contacting the product stream with an alkanolamine to convert at least a portion of the carbon disulfide to a higher boiling point product, and (ii) removing at least a portion of the higher boiling point product from the product stream to form a purified sulfide stream. Generally, the features of the processes (e.g., the components and/or features of the product stream, the alkanolamine, the components and/or features of the purified sulfide stream, and the process conditions under which the product stream and alkanolamine are contacted, among others) are independently described herein, and these features can be combined in any combination to further describe the disclosed purification processes.

The amount of the sulfide compound present in the product stream is not particularly limited, although the sulfide compound generally constitutes the vast majority of the product stream, for instance, at least about 80 wt. %, at least about 85 wt. %, or at least about 90 wt. %, and more often, the product stream contains at least about 95 wt. %, at least about 98 wt. %, at least about 99 wt. %, or at least about 99.9 wt. %, of the sulfide compound. Representative ranges for the amount of the sulfide compound in the product stream can include from about 90 wt. % to about 99.99 wt. %, from about 95 wt. % to about 99.99 wt. %, from about 98 wt. % to about 99.9 wt. %, or from about 99 wt. % to about 99.9 wt. %. Thus, the product stream can be a relatively pure sulfide product stream containing only trace amounts of certain impurities, and the impurities can be difficult to remove by conventional purification processes.

In addition to the sulfide compound, the product stream can contain an unacceptably high amount of carbon disulfide. In some aspects, the product stream prior to step (i) can contain from about 100 ppm to about 10,000 ppm (by weight) of carbon disulfide, such as from about 250 ppm to about 5000 ppm, from about 500 ppm to about 10,000 ppm, from about 1000 ppm to 5000 ppm, or from about 2000 ppm to about 4000 ppm, although not limited thereto. In other aspects, the amount of carbon disulfide present in the product stream can be at least about 100 ppm, at least about 250 ppm, at least about 500 ppm, at least about 1000 ppm, or at least about 2000 ppm (by weight).

The product stream also can contain additional impurities and by-products from the production of the sulfide compound. Such additional impurities can further complicate the purification of the product stream. As an example, the product stream can comprise hydrogen sulfide and/or water prior to step (i). Where present, the product stream can contain an amount of $H_2S$ in a range from about 1 ppm to about 100 ppm, or from about 5 ppm to about 75 ppm. Similarly, the product stream can contain an amount of water in a range from about 10 ppm to about 1000 ppm, from about 50 ppm to about 500 ppm, or from about 10 ppm to about 100 ppm. In certain aspects, the amount of $H_2S$ and/or water in the purified sulfide stream independently can be unchanged, less than, or greater than that in the product stream containing the sulfide compound.

In step (i), the product stream can be contacted with an alkanolamine to convert at least a portion of the $CS_2$ to a higher boiling point product. Any suitable temperature and pressures conditions can be used for step (i). The temperature is not particularly limited, and generally can be any temperature sufficient and practical for the alkanolamine to react with the $CS_2$ and form a higher boiling point product. For instance, step (i) can be conducted without heating, at ambient temperature. In other aspects, the temperature of step (i) can be in a range from about 15° C. to about 85° C., from about 20° C. to about 70° C., from about 25° C. to about 60° C., or from about 30° C. to about 45° C. Similarly, the pressure in step (i) is not particularly limited, but in some aspects, can be such that each component of the product stream remains a liquid at the operating temperature. Thus, step (i) can be conducted at ambient pressure or a pressure of at least 5 psig (34 kPag), at least 10 psig (69 kPag), at least 15 psig (103 kPag), at least 20 psig (138 kPag), at least 25 psig (172 kPag), at least 30 psig (207 kPag), at least 40 psig (276 kPag), at least 50 psig (345 kPag), at least 60 psig (414 kPag), at least 80 psig (551 kPag), or at least 100 psig (689 kPag). In some aspects, step (i) can be conducted at a pressure in a range from ambient pressure to about 100 psig (689 kPag), or from about 5 psig (34 kPag) to about 60 psig (414 kPag).

If desired, a diluent can be used in step (i), such that the product stream is contacted with the alkanolamine in a diluent. Suitable diluents contemplated herein include alcohol, ether, and hydrocarbon solvents. In certain aspects, the diluent can comprise an alcohol, such as $C_1$ to $C_3$ alcohol (e.g., methanol, ethanol, or isopropanol). Any suitable amount of the diluent can be used, and when a diluent is present, the weight ratio of alkanolamine:diluent can range from about 99:1 to about 10:90, from about 95:5 to about 25:75, from about 85:15 to about 50:50, or from about 90:10 to about 70:30.

Any suitable relative amount of the alkanolamine and carbon disulfide can be used in step (i). For instance, the molar ratio of alkanolamine:$CS_2$ can be in a range from about 1:1 to about 20:1, from about 1:1 to about 6:1, from about 1.5:1 to about 10:1, from about 1.5:1 to about 5:1, from about 2:1 to about 6:1, or from about 3:1 to about 10:1. Often, it can be beneficial to use an excess of the alkanolamine relative to the amount of carbon disulfide impurity in the product stream.

Similarly, the alkanolamine can be added to the product stream in any suitable amount relative to the total weight of the product stream. In some aspects, the amount of the alkanolamine added to the product stream can be in a range from about 0.01 to about 5 wt. %, from about 0.1 to about 3 wt. %, from about 0.1 to about 2 wt. %, from about 0.2 to about 1 wt. %, from about 0.3 to about 0.9 wt. %, or from about 0.4 to about 1.5 wt. %, based on the weight of the product stream.

Optionally, the amount of $CS_2$ present in the product stream can be monitored, and the amount of the alkanolamine added to the product stream can be controlled accordingly. For instance, the processes disclosed herein can further comprise the steps of determining (or measuring) the concentration of the $CS_2$ present in the product stream, and adjusting the amount of alkanolamine contacted with the product stream based on the concentration of $CS_2$ in the product stream (the determined concentration). In such aspects, a target ratio of alkanolamine:$CS_2$ can be efficiently maintained to ensure substantially complete conversion of the $CS_2$ during step (i) of the process, regardless of upward/downward spikes in the concentration of $CS_2$ in the product stream. This methodology also can reduce costs by avoiding excess addition of the alkanolamine, when it is not needed.

Step (i) can be conducted for any suitable period of time, generally for a time period sufficient for substantially all of the $CS_2$ to be converted to the higher boiling point product. Although the particular time can vary based on temperature and alkanolamine:$CS_2$ molar ratio, among other variables, step (i) often can be conducted for a time period in a range from about 0.5 min to about 24 hr, from about 1 min to about 24 hr, from about 2 min to about 12 hr, from about 2 min to about 2 hr, from about 2 min to about 30 min, or from about 5 min to about 1 hr, and the like. To improve the contact between the alkanolamine and the $CS_2$ components, which are present in small amounts in step (i), the mixture of the product stream (containing $CS_2$) and the alkanolamine can be vigorously agitated in step (i).

The conditions and components disclosed herein can be combined in any manner to effectuate an efficient conversion of at least a portion of the $CS_2$ present in the product stream. Generally, at least about 40 wt. % of the $CS_2$ in the product stream is converted to a higher boiling point product, and more often, at least about 50 wt. %, at least about 60 wt. %, at least about 70 wt. %, at least about 80 wt. %, at least about 85 wt. %, at least about 90 wt. %, at least about 95 wt. %, or at least about 98 wt. %, and in some instances, at least about 99 wt. %, at least about 99.9 wt. %, or at least about 99.99 wt. %. Thus, typical amounts of the $CS_2$ in the product stream that are converted into a higher boiling point product can range from about 60 wt. % to about 99.99 wt. %, from about 90 wt. % to about 99.9 wt. %, or from about 98 wt. % to about 99.99 wt. %.

The higher boiling point product (or products) formed in step (i) can be dependent on the structure of the alkanolamine and the reaction that takes place with $CS_2$. In some aspects, the higher boiling point product can comprise a cyclic product, while in other aspects, the higher boiling point product can comprise a heterocyclic organic compound, e.g., with oxygen, nitrogen, sulfur, or any combination thereof, in the ring. Regardless of the structure of the higher boiling point product (or products), beneficially, the "higher boiling point product" has a higher boiling point (at 1 atm, normal boiling point) than that of $CS_2$ (which has a normal boiling point of ~46-47° C.). Additionally, the higher boiling point product can have a higher boiling point (normal boiling point) than that of the sulfide compound in the product stream (e.g., dimethyl sulfide has a normal boiling point of ~35-41° C.). A larger difference between the respective boiling points of the higher boiling point product (or products) and the sulfide compound in the product stream can facilitate easier separation or removal of the higher boiling point product from the product stream in step (ii), e.g., via distillation. Thus, in certain aspects, the normal boiling point of the higher boiling point product can be at least about 20° C. greater, at least about 30° C. greater, at least about 40° C. greater, at least about 50° C. greater, at least about 75° C. greater, or at least about 100° C. greater, than the normal boiling point of $CS_2$ and/or the normal boiling point of the sulfide compound.

Additionally, it can be beneficial for the higher boiling point product (or products) to be a liquid (not a solid) and to remain in the liquid state at a particular set of process conditions, such as at standard temperature and pressure (STP, 1 atm and 20° C.); additionally or alternatively, a liquid at 0° C. and 2 atm, additionally or alternatively, a liquid at −10° C. and 2 atm.

In addition to a higher boiling point product (or products), the conversion of $CS_2$ in step (i) also can produce lower boiling point byproducts, such as $H_2S$. However, trace amounts of $H_2S$ resulting from step (i) would not be problematic, since $H_2S$ is a gas at STP, and therefore can be easily removed from the product stream.

As a non-limiting example of step (i) in which the alkanolamine is ethanolamine, and the sulfide compound is dimethyl sulfide, step (i) can produce the products shown in Scheme I below. Several higher boiling point products with boiling points much greater than that of both the sulfide compound and $CS_2$ are produced.

Scheme I. Conversion of $CS_2$ to various higher boiling point products and byproducts in a product stream containing dimethyl sulfide.

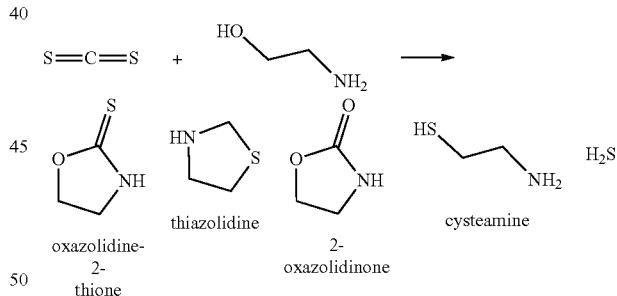

oxazolidine-2-thione    thiazolidine    2-oxazolidinone    cysteamine

Thus, the higher boiling point product can comprise a heterocyclic organic compound. For instance, ƒ1-hydroxy amines can form stabile 5-membered cyclic products that incorporate both the nitrogen and oxygen of the alkanolamine compound within the ring through sequential addition to the electrophilic carbon of $CS_2$. The higher boiling point product can contain oxygen, nitrogen, or sulfur, in any arrangement within the ring of a cyclic product.

Referring now to step (ii), in which at least a portion of the higher boiling point product is removed or separated from the product stream to form the purified sulfide stream. Any suitable technique can be used to remove the higher boiling point product (or products) from the product stream. Such techniques can include filtration, extraction, evaporation, distillation, and the like, or any combination of two or more of these techniques. For instance, the higher boiling point product can be removed from the product stream using distillation to form the purified sulfide stream. In such aspects, the product stream containing the sulfide compound can proceed to a distillation kettle where the sulfide compound can be distilled through a column to an overhead condenser, leaving the higher boiling point product(s) in the refluxing distillation kettle below. In this manner, the product stream proceeds from the distillation kettle through the column, and forms the purified sulfide stream, while the higher boiling point product(s) can be removed from the product stream and remain in the distillation kettle.

In aspects where step (ii) comprises distillation, the distillation can be performed at any temperature and pressure conditions suitable for the removal of the higher boiling point product from the product stream, and to suitably result in a purified sulfide stream. For instance, the distillation pressure can be in a range from ambient to about 100 psig (689 kPag), from about 20 psig to about 50 psig (138 kPag to 345 kPag), or from about 5 psig to about 30 psig (35 kPag to 207 kPag). The distillation temperature (at the top of the column) can be in a range from about 25° C. to about 120° C., from about 35° C. to about 125° C., from about 65° C. to about 120° C., or from about 85° C. to about 120° C., and can depend on the particular distillation pressure and the specific sulfide compound in the product stream and the specific higher boiling point product(s).

In an embodiment where step (ii) comprises distillation, the process can occur in a distillation tower (or distillation column), such as a packed tower. More specifically, the distillation tower can contain packing that facilitates mass transfer between the vapor and liquid phases in the distillation tower. In an alternative embodiment, the distillation tower can contain trays to facilitate the separation. As mentioned previously, the purified sulfide stream can exit the top of the tower. In an embodiment, the alkanolamine can be added to the distillation tower at a point at or below at least one layer of packing. Alternatively, the alkanolamine can be added continuously to the feed (the impure product stream) to the distillation tower and is mixed into the feed via an in-line static mixer. In an embodiment, the temperature at the point of alkanolamine addition is above 37° C.

In an embodiment, the function of the distillation tower is to remove $CS_2$ impurities from dimethyl sulfide (DMS). In an embodiment, the purified DMS contains less than 20 ppm by weight $CS_2$, or alternatively, less than 1 ppm (by weight) $CS_2$.

In an embodiment, the alkanolamine is ethanolamine (monoethanolamine (MEA)). In another embodiment, the ethanolamine is diethanolamine (DEA). The alkanolamine can be mixed with a solvent before it is added either directly to the distillation tower or mixed with the distillation tower feed. Any suitable solvent that is miscible with the alkanolamine may be used. For example, solvents such as water, methanol, isopropanol, acetone, methyl ethyl ketone, or glycerol may be suitable. However, for certain alkanolamines, such as MEA, certain solvents such as water and methanol can form azeotropes with DMS or cause unwanted phase separations. In an embodiment, the alkanolamine is mixed with isopropanol before being added to the distillation tower or to the distillation tower feed.

In yet another embodiment, the amount of alkanolamine added (either to the distillation tower or to the distillation tower feed) is controlled via a feedback control loop. A carbon disulfide removal system 100 is shown in FIG. 1, in which an alkanolamine feed 102 can be added either directly to distillation tower 110 via inlet 102A, or alternatively, alkanolamine feed stream 102B can be mixed with impure sulfide product stream 101 to form distillation tower feed stream 105. In instances where the alkanolamine is added to the tower 110 only via inlet 102A, product stream 101 and feed stream 105 are the same.

As shown in FIG. 1, the amount of alkanolamine added to distillation tower 110 can be controlled by measuring the concentration of $CS_2$ in overhead stream 155 leaving the distillation tower. In an embodiment, the concentration of $CS_2$ can be measured using any suitable analytical instrument 120, such as online analyzer (e.g., gas chromatograph) equipped with a sulfur chemiluminescence detector. If the measured $CS_2$ concentration is higher than desired, then a feedback control loop using flow indicator controller 125A will signal for valve 122A to open and more alkanolamine will be added via inlet 102A, in circumstances where the alkanolamine is fed directly to the tower. Moreover, if the measured $CS_2$ concentration is lower than desired, then the feedback control loop will signal for valve 122A to close. In like manner, a similar control scheme using flow indicator controller 125B and value 122B can be used if the alkanolamine is mixed with impure sulfide product stream 101. The amount of alkanolamine added can depend on the flow rate of the impure sulfide product stream 101, as measured by flow indicator 130, and a ratio indicator controller 135 can be used to control and optimize the amount of alkanolamine (relative to the sulfide product stream) required to achieve the desired concentration of $CS_2$ in stream 155 leaving the top of the distillation tower.

If desired, overhead stream 155 can be passed through heat exchanger 150, thereby forming purified sulfide stream 165, while some of the overhead stream 155 can be refluxed to the tower via stream 175. The heavies stream 145 exits the bottom of the tower and also can be passed through heat exchanger 140.

The distillation tower capable of producing a purified sulfide stream, such as a DMS stream containing less than 20 ppm by weight, or alternatively, 1 ppm by weight or less $CS_2$ can be part of an integrated system for producing mercaptans such as methyl mercaptan (MeSH) from the reaction of methanol and $H_2S$. In addition to producing mercaptans, the process can also produce dimethyl sulfide (DMS) and $CS_2$, as well as other products and byproducts.

Figure 2:
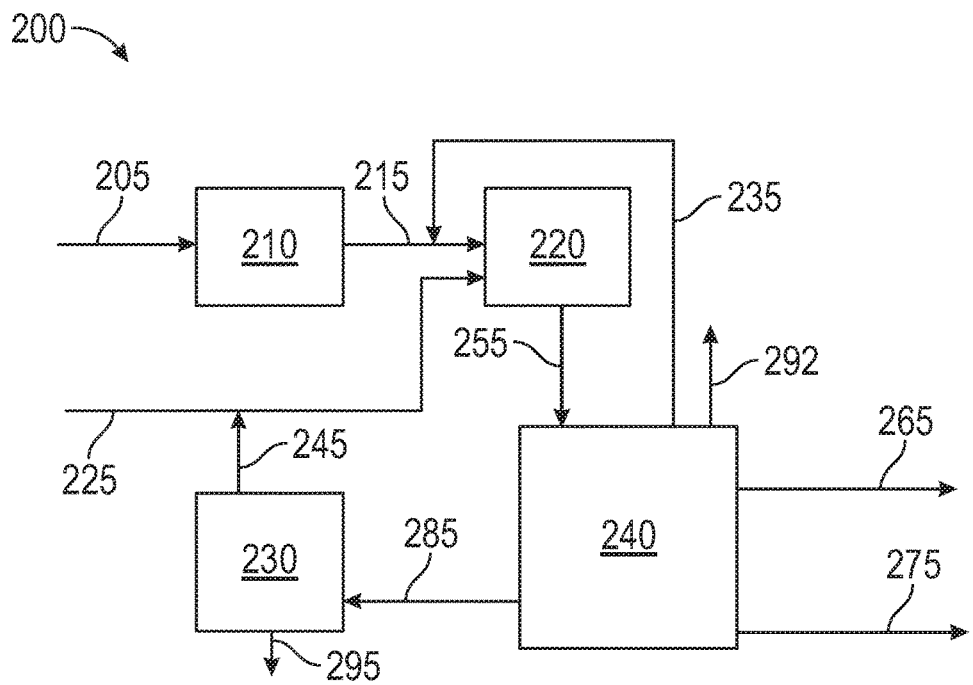
FIG. 2 illustrates a mercaptan and sulfide production system consistent with another aspect of the present invention.

As shown in FIG. 2, system 200 can include (but is not limited to) the following: i) a methanol (or other alcohol, such as ethanol) feed stream 225; ii) an $H_2S$ feed stream 205; iii) a mercaptan synthesis unit 220; iv) and a product purification and fractionation unit 240 where the MeSH product stream 265 is separated from the DMS product stream 275 and vent stream 292. In an embodiment, the mercaptan synthesis unit 220 can be a catalytic flow reactor. In another embodiment, excess (recycle) $H_2S$ 235 is separated from reactor effluent 255, and stream 235 can be combined with feed inlet 215 to the mercaptan synthesis unit 220. $H_2S$ feed stream 205 is passed through compressor 210 prior to entering the mercaptan synthesis unit.

The product purification and fractionation unit 240 can include a phase effluent separator and one or more distillation towers. Stream 285 can be sent to a water purification unit 230 to separate a water stream 295 from a methanol recycle stream 245 (which also may contain some $H_2S$), and stream 245 can be combined with methanol feed stream 225. In an embodiment, DMS product stream 275 containing $CS_2$ (and other impurities) is produced as an overhead product from the last column in the series of columns in unit 240.

In a further embodiment, the DMS product stream 275 (containing the $CS_2$ impurity) leaving the product purification and fractionation unit 240 of the mercaptan and sulfide synthesis system 200 is then further treated to remove $CS_2$ via the addition of an alkanolamine. In an embodiment, carbon disulfide removal system 100, as depicted in FIG. 1, is integrated into system 200 downstream of the product purification and fractionation unit.

In a further embodiment, the highly purified DMS containing less than 20 ppm (by weight), less than 10 ppm (by weight), less than 5 ppm (by weight), or less than 1 ppm (by weight) $CS_2$ has several subsequent uses. In one embodiment, purified DMS containing less than 20 ppm (by weight) can be used in naphtha (or ethane or propane) steam cracking furnaces used for olefins (ethylene) production. The addition of DMS prevents catalytic coking of the furnace tubes used in olefins production and extends the duration between furnace decokes; however, the DMS must be low in $CS_2$ content in order to prevent the $CS_2$ from accumulating in the $C_5+$ product fraction. In an alternative embodiment, very high purity DMS (e.g., less than 1 ppm by weight $CS_2$) can be used as a reagent to make dimethyl sulfoxide (DMSO).

As discussed above, the removal of $CS_2$ from product streams containing a sulfide compound can be problematic due to the components having similar chemical and physical characteristics. Thus, the effectiveness of the removal step applied directly to $CS_2$ can be limited, with respect to both the relative amount of the $CS_2$ removed (compared to an amount of $CS_2$ present in the product stream) and the actual amount of $CS_2$ removed. Moreover, as the levels of $CS_2$ in the product stream are reduced, it can become increasingly difficult to remove any significant portion of $CS_2$ from the product stream where the chemical and/or physical properties are similar. In contrast, in the processes disclosed herein, all or substantially all of the $CS_2$ can be removed from the product stream to form a purified sulfide stream in an efficient manner via the use of an appropriate amount of alkanolamine to react with the $CS_2$, resulting in higher boiling point products that are easily removed via conventional distillation or other suitable technique.

Generally, at least about 40 wt. % of the higher boiling point product (or products) in the product stream is removed in step (ii), and more often, at least about 50 wt. %, at least about 60 wt. %, at least about 70 wt. %, at least about 80 wt. %, at least about 85 wt. %, at least about 90 wt. %, at least about 95 wt. %, or at least about 98 wt. %, and in some instances, at least about 99 wt. %, at least about 99.9 wt. %, or at least about 99.99 wt. %. Thus, typical amounts of the higher boiling point product that are removed from the product stream can range from about 60 wt. % to about 99.99 wt. %, from about 80 wt. % to about 99.99 wt. %, or from about 90 wt. % to about 99.99 wt. %.

As a result, the purified sulfide stream can have exceptional purity of the sulfide compound, generally far in excess of methods in which $CS_2$ is attempted to be removed directly (e.g., by fractional distillation). The ratio of the concentration (ppm by weight) of $CS_2$ in the product stream prior to step (i) to the concentration (ppm by weight) of $CS_2$ in the purified sulfide stream can be at least about 10:1, at least about 25:1, or at least about 100:1, and in some aspects, at least about 250:1, at least about 500:1, or at least about 1000:1. With regard to the purity of the sulfide compound, the purified sulfide streams formed by the processes disclosed herein can contain amounts of $CS_2$ of less than or equal to about 200 ppm, less than or equal to about 150 ppm, less than or equal to about 100 ppm, less than or equal to about 75 ppm, less than or equal to about 50 ppm, less than or equal to about 25 ppm, less than or equal to about 10 ppm, or less than or equal to about 1 ppm (by weight). Hence, the amount of $CS_2$ in the purified sulfide stream can range from about 1 ppm to about 100 ppm, from about 1 ppm to about 50 ppm, or from about 1 ppm to about 10 ppm (by weight). With respect to the overall purity of the sulfide compound in purified sulfide stream formed in step (ii), in certain aspects, the amount of the sulfide compound in the purified sulfide stream can be at least about 99 wt. %, at least about 99.9 wt. %, at least about 99.99 wt. %, at least about 99.995 wt. %, or at least about 99.999 wt. %.

Optionally, the amount of $CS_2$ present in the purified sulfide stream can be monitored, and the amount of the alkanolamine added to the product stream can be controlled accordingly. For instance, the processes disclosed herein can further comprise the steps of determining (or measuring) the concentration of the $CS_2$ present in the purified sulfide stream, and adjusting the amount of alkanolamine contacted with the product stream based on the concentration of $CS_2$ in the purified sulfide stream (the determined concentration). In such aspects, a target ratio of alkanolamine:$CS_2$ can be efficiently maintained to ensure that less than or equal to about 100 ppm, less than or equal to about 25 ppm, less than or equal to about 10 ppm, or no measurable amount of the $CS_2$ is present in the purified sulfide stream, regardless of upward/downward spikes in the concentration of $CS_2$ in the product stream.

Sulfide Compounds

Generally, the product stream can contain any suitable sulfide compound in which carbon disulfide also is present as an impurity, and thus may be benefit from the purification processes described herein. In some aspects, for instance, the product stream can contain a sulfide compound having formula (I):

$$R^1\text{—}S\text{—}R^2 \qquad (I).$$

In formula (I), $R^1$ and $R^2$ independently can be a $C_1$ to $C_{18}$ substituted or unsubstituted, cycloalkyl group or linear or branched alkyl group. It is contemplated that $R^1$ and $R^2$ can be the same or different. When $R^1$ and $R^2$ are the same, the sulfide compound is symmetrical, and when $R^1$ and $R^2$ are different, the sulfide compound is asymmetrical.

$R^1$ in formula (I) can be a $C_1$ to $C_{18}$ substituted or unsubstituted, cycloalkyl group or linear or branched alkyl group. In one aspect, for example, $R^1$ can be a $C_1$ to $C_{14}$ substituted or unsubstituted, cycloalkyl group or linear or branched alkyl group, while in another aspect, $R^1$ can be a $C_1$ to $C_{12}$ substituted or unsubstituted, cycloalkyl group or linear or branched alkyl group, and in yet another aspect, $R^1$ can be a $C_1$ to $C_8$ substituted or unsubstituted, cycloalkyl group or linear or branched alkyl group. Consistent with aspects of the present invention, $R^1$ can be a cycloalkyl group; alternatively, $R^1$ can be a linear alkyl group; or alternatively, $R^1$ can be a branched alkyl group. Regardless of whether $R^1$ is a cyclic, linear, or branched alkyl group, $R^1$ can be unsubstituted, or can be substituted with any suitable substituent, any suitable number of substituents, and at any suitable position(s) that conforms to the rules of chemical valence.

$R^1$ can be a $C_1$ to $C_{18}$ linear or branched alkyl group in certain aspects of this invention. Thus, $R^1$ can be a $C_1$ to $C_{14}$ linear or branched alkyl group, a $C_1$ to $C_{12}$ linear or branched alkyl group, a $C_1$ to $C_8$ linear or branched alkyl group, or a $C_1$ to $C_6$ linear or branched alkyl group. Accordingly, in some aspects, $R^1$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a decyl group, or a dodecyl group.

In other aspects, the alkyl group which can be $R^1$ in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group; alternatively, a methyl group, an ethyl group, or an iso-propyl group; alternatively, a methyl group or an ethyl group; alternatively, a methyl group; alternatively, an ethyl group; alternatively, a n-propyl group; alternatively, an iso-propyl group; alternatively, a n-butyl group; alternatively, an iso-butyl group; alternatively, a sec-butyl group; alternatively, a tert-butyl group; alternatively, a n-pentyl group; alternatively, an iso-pentyl group; alternatively, a sec-pentyl group; alternatively, a neopentyl group; alternatively, a tert-amyl group; alternatively, a n-hexyl group; alternatively, a n-heptyl group; alternatively, a n-octyl group; or alternatively, or a n-dodecyl group.

$R^1$ can be a cycloalkyl group in certain aspects of this invention. Thus, $R^1$ can be a $C_3$ to $C_{18}$ cycloalkyl group, a $C_4$ to $C_{12}$ cycloalkyl group, a $C_4$ to Cm cycloalkyl group, or a $C_5$ to $C_8$ cycloalkyl group. Accordingly, in some aspects, $R^1$ can be a cyclobutyl group, a cyclopentyl group, a cyclohexyl group, a cycloheptyl group, or a cyclooctyl group; alternatively, a cyclobutyl group; alternatively, a cyclopentyl group; alternatively, a cyclohexyl group; alternatively, a cycloheptyl group; or alternatively, a cyclooctyl group.

In accordance with another aspect of this invention, any alkyl group disclosed herein (cycloalkyl, linear alkyl, or branched alkyl) can be substituted with one or more substituents. Each non-hydrogen substituent(s) for the substituted alkyl group independently can be a $C_1$ to Cis hydrocarbyl group; alternatively, a $C_1$ to $C_8$ hydrocarbyl group; or alternatively, a $C_1$ to $C_6$ hydrocarbyl group. Thus, the hydrocarbyl substituent can be a benzyl group, a phenyl group, a tolyl group, or a xylyl group, and the like, and, therefore, $R^1$ can be, for instance, a phenyl-substituted alkyl group. Additionally, the hydrocarbyl substituent can be a $C_1$ to $C_6$ linear or branched alkyl group and, therefore, $R^1$ can be, for instance, an alkyl-substituted cycloalkyl group, such as a methylcyclohexyl group.

An illustrative non-hydrocarbon substituent that can be present on any alkyl group disclosed herein (cycloalkyl, linear alkyl, or branched alkyl) is a hydroxy group (—OH group). Thus, $R^1$ can be a methyl alcohol or methanol group (—$CH_2OH$), an ethyl alcohol or ethanol group (—$CH_2CH_2OH$), a propanol group, a butanol group, a pentanol group, a hexanol group, and so forth.

Referring now to $R^2$ in formula (I), $R^2$ can be any $C_1$ to Cis substituted or unsubstituted, cycloalkyl group or linear or branched alkyl group disclosed herein for $R^1$. Thus, for example, $R^2$ can be any cycloalkyl group, linear alkyl group, or branched alkyl group disclosed herein, and further, $R^2$ can be unsubstituted, or can be substituted with any suitable substituent or any substituent disclosed herein, any suitable number of substituents, and at any suitable position(s) that conforms to the rules of chemical valence.

In aspects where the sulfide compound is asymmetrical, the sulfide compound can be methyl ethyl sulfide, methyl iso-propyl sulfide, methyl dodecyl sulfide, ethyl octyl sulfide, n-pentyl n-heptyl sulfide, and the like, as well as any combination thereof. In certain aspects, the sulfide compound can be methyl ethyl sulfide. In aspects where the sulfide compound is symmetrical, the sulfide compound can be dimethyl sulfide, diethyl sulfide, di-n-propyl sulfide, di-iso-propyl sulfide, di-n-butyl sulfide, di-n-pentyl sulfide, di-n-hexyl sulfide, di-n-heptyl sulfide, di-n-octyl sulfide, di-n-dodecyl sulfide, and the like, as well as any combination thereof. In certain aspects, the sulfide compound can be dimethyl sulfide.

Certain aspects of the processes disclosed herein may be applicable to sulfide compounds having particular characteristics, e.g., molecular weight, polarity, boiling point, etc. For instance, it can be beneficial for the sulfide compound to be a liquid (not a solid) and to remain in the liquid state at a particular set of process conditions, such as at standard temperature and pressure (STP, 1 atm and 20° C.). Thus, sulfide compounds suitable for the processes disclosed herein can be a liquid at STP, and beneficially remain a liquid at 0° C. and 2 atm, and/or remain a liquid at −10° C. and 2 atm. While not limited thereto, the sulfide compound can have a normal boiling point (at 1 atm) of at least about 30° C., at least about 50° C., at least about 70° C., or at least about 90° C. Additionally or alternatively, the sulfide compound can have a normal boiling point within 100° C., within 50° C., within 30° C., or within 10° C., of that of carbon disulfide (which has a normal boiling point of −46-47° C.).

Alkanolamines

Aspects of this invention are directed to processes to purify a product stream containing a sulfide compound. Such processes can comprise contacting the product stream with any suitable alkanolamine to convert at least a portion of $CS_2$ in the product stream to a higher boiling point product. For instance, the alkanolamine can react with $CS_2$ present in the product stream and convert the $CS_2$ to a higher boiling point product, which can be more readily removed or separated from the product stream, such as via distillation. Significantly, the reactivity of the alkanolamine can be relatively low with respect to the sulfide compound as compared to its reactivity with carbon disulfide, such that the alkanolamine can preferentially react with trace amounts of carbon disulfide even in the presence of a large excess of the sulfide compound. In some aspects, the alkanolamine can be selected such that it does not react with the particular sulfide compound in the product stream.

Alkanolamines encompassed herein include compounds having both a hydroxy group and an amine group. The alkanolamine can be a $C_1$ to $C_{18}$ alkanolamine; alternatively, a $C_2$ to $C_{18}$ alkanolamine; alternatively, a $C_1$ to $C_{12}$ alkanolamine; alternatively, a $C_2$ to $C_{12}$ alkanolamine; alternatively, a $C_2$ to $C_8$ alkanolamine; or alternatively, a $C_2$ to $C_6$ alkanolamine. In one aspect, the alkanolamine can be a monoalkanolamine (one hydroxy group), illustrative and non-limiting examples of which can include methanolamine, ethanolamine, n-propanolamine, n-isopropanolamine, n-butanolamine, isobutanolamine, and the like, as well as combinations thereof. In another aspect, the alkanolamine can be a dialkanolamine (two hydroxy groups), illustrative and non-limiting examples of which can include diethanolamine, diisopropanolamine, and the like, or a combination thereof. In yet another aspect, the alkanolamine can be a trialkanolamine (three hydroxy groups), a non-limiting example of which is triethanolamine. Combinations of alkanolamines can be used in the disclosed processes, such as a mixture of a monoalkanolamine and a dialkanolamine, a mixture of two different monoalkanolamines, and so forth.

The amine group in the alkanolamine can be a primary amine group, a secondary amine group, or a tertiary amine group. In particular aspects of this invention, the alkanolamine contains a primary amine. The alkanolamine can be linear or branched, and substituted or unsubstituted, as would be recognized by a skilled artisan.

Additionally, the alkanolamine can contain, in some aspects, a heteroatom-containing linking group between the amine and hydroxy group(s). For example, the heteroatom can be oxygen or sulfur, and thus the heteroatom-containing linking group can be an ether or thioether. This is illustrated by the representative alkanolamine shown below—2-(2-aminoethoxy)ethanol—which contains an ether group between the amine and hydroxy group.

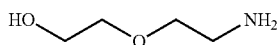

Other suitable heteroatom-containing linking groups are also contemplated herein, wherein the linking group can comprise any linking group formed by substituting one or more carbon atoms of any hydrocarbon linking group (e.g., $C_2$ to $C_{18}$) disclosed herein with one more heteroatoms. Heteroatomic linking groups can be linear or branched, and substituted or unsubstituted, as described above in relation to $R^1$ and $R^2$ of the sulfide compound.

Another non-limiting class of alkanolamines suitable for the processes contemplated herein includes β-hydroxy amines, according to formula (II):

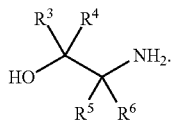

(II)

In certain aspects of the processes contemplated herein, β-hydroxy amines can be particularly reactive with carbon disulfide in a product stream due to their ability to form stable cyclic byproducts through reactions with carbon disulfide that can be effectively irreversible. Without being bound by theory, such aspects can convert undesired carbon sulfide in the product stream to stable byproducts that can be more easily removed from the product stream. In certain aspects, β-hydroxy amines of formula (II) can produce heterocyclic products by incorporating the relatively reactive carbon of the carbon disulfide into a 5-membered heterocyclic ring, as well as other reaction products such as those disclosed herein (e.g., $H_2S$, cysteamine, etc.).

In formula (II) above, $R^3$-$R^6$ independently can be H or a $C_1$ to $C_{12}$ alkyl group; alternatively, H or a $C_1$ to $C_6$ alkyl group; alternatively, H or a $C_2$ to $C_{12}$ alkyl group; alternatively, H or a $C_2$ to $C_6$ alkyl group; or alternatively, H or a $C_1$ to $C_4$ alkyl group. Thus, in some aspects, $R^3$-$R^6$ in formula (II) independently can be H, a methyl group, an ethyl group, a propyl group, a butyl group, a pentyl group, or a hexyl group.

Similar to the sulfide compounds, suitable alkanolamines for the processes disclosed herein can have particular beneficial characteristics, including reactivity with $CS_2$, the ability to form certain higher boiling point products, polarity, boiling point, etc. For instance, it can be beneficial for the alkanolamine to be a liquid (not a solid) and to remain in the liquid state at a particular set of process conditions, such as at standard temperature and pressure (STP, 1 atm and 20° C.). Thus, alkanolamines suitable for the processes disclosed herein can be a liquid at STP, and beneficially remain a liquid at 0° C. and 2 atm, and/or remain a liquid at −10° C. and 2 atm.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

A gas chromatography (GC) method was used to determine the ppm (by weight) of carbon disulfide. Samples were analyzed using a Sulfur Chemiluminescence Detector (SCD) equipped with a DB-1 column (60 m×320 μm×1 μm). The initial temperature was set to 40° C. for 4 minutes, then ramped to 60° C. at 5° C./rain, then to 170° C. at 30° C./min. It was found that a sulfur specific detector was necessary for $CS_2$ levels of less than 50 ppm in dimethyl sulfide; a FID detector was inadequate.

Comparative Example

The comparative example utilized conventional distillation processes for purifying a product stream containing dimethyl sulfide. Two distillation columns were used. Columns T-3 and T-2 were packed columns: T-3 had 63 theoretical stages and T-2 had 40 theoretical stages, and about 75 and 50 feet of packing, respectively. The overhead distillate from column T-3 was the feed to column T-2. Tables I-II summarize the conditions in Column T-2 and Column T-3, respectively, and results of the comparative distillation process taken at roughly six-hour intervals over the course of about ten days. As is shown, the temperature and pressure were varied in an effort to improve the separation of the carbon disulfide impurity from dimethyl sulfide.

Referring first to Table II and comparing the amount of $CS_2$ in the overhead (average ~1000 ppm) versus in the kettle (average 4000), it can be concluded that while a significant amount of $CS_2$ can be removed in column T-3, it is very difficult to consistently produce an overhead stream containing less than 1000 ppm by weight of $CS_2$.

Referring now to Table I and comparing the amount of $CS_2$ in the overhead versus in the kettle, it can be concluded that the amount of $CS_2$ removed in column T-2 is highly variable, and in some cases, distillation in column T-2 was completely ineffective at reducing the amount of $CS_2$. Significantly, there was no data in these experiments to indicate that a purified stream containing less than 250 ppm by weight of $CS_2$ (or less than 100 ppm) could possibly be achieved using distillation.

In sum, distillation was not able to efficiently separate $CS_2$ from a dimethyl sulfide product stream in order to achieve a high purity dimethyl sulfide stream, for example, with $CS_2$ levels of much less than 500 ppm, such as 250 ppm or less, 100 ppm or less, or 20 ppm or less.

Examples 1-12

Examples 1-12 were conducted with samples of dimethyl sulfide having known concentrations of $CS_2$. In each experiment, an amount of dimethyl sulfide "product stream" was mixed with an alkanolamine, and the concentration of $CS_2$ was monitored for up to 150 minutes. Various loadings of the alkanolamine were examined, as well as various contacting temperatures. It was observed that the conversion of $CS_2$ occurred quickly in most cases, proceeding either to completely remove $CS_2$ from the product stream, or stabilize within about 30 minutes.

Table III summarizes the results of the conversion reactions of Examples 1-12, and shows the starting concentrations of $CS_2$ around 2000-2700 ppm (by weight), and the final concentration of $CS_2$ after a set period of time. Surprisingly, the molar ratio of the alkanolamine:$CS_2$ that allowed the conversion to proceed quickly to completion in each example was greater than 1:1. Thus, a simple stoichiometric amount of alkanolamine based on the amount of $CS_2$ present in the sulfide product stream may not be sufficient in all cases to convert the $CS_2$ to a higher boiling point product, thereby removing it from the product stream. In Example 1, a dimethyl sulfide product stream having a $CS_2$ concentration of 2088 ppm was mixed with 0.3 wt. % monoethanolamine (based on the weight of the dimethyl sulfide product stream), or an alkanolamine:$CS_2$ molar ratio of 1.8:1. While the amount of $CS_2$ present in the mixture decreased over the course of the reaction, the final concentration of $CS_2$ in the mixture was significant even after 150 minutes. In comparison, increasing the amount of monoethanolamine to 0.5 wt. % (Example 2) reduced the amount of $CS_2$ drastically, to 97 ppm after 120 minutes. At 36° C., Example 3 used monoethanolamine at a concentration of 0.7 wt. % and completely converted the $CS_2$ present in the mixture within less than 30 minutes.

Examples 4-7 were conducted at 36° C. and produced similar results to Examples 1-3. Notably, the amount of monoethanolamine needed for complete conversion of the $CS_2$ appears to scale with the amount of $CS_2$ present, despite alkanolamine:$CS_2$ ratios of less than about 3:1 not fully converting the $CS_2$ present in the product mixture to higher boiling point products. Particularly, Example 4 used a loading of 0.3 wt. %, and the $CS_2$ level dropped to 847 ppm after 30 minutes, Example 5 used a loading of 0.5 wt. %, and the $CS_2$ level dropped to 375 ppm after 60 minutes, while Example 6 used a loading of 0.71 wt. %, and almost converted all the $CS_2$ within 30 minutes, leaving only a small amount of $CS_2$ remaining in the product mixture (46 ppm). In contrast, increasing the monoethanolamine loading to 0.85 wt. % (Example 7) resulted in the complete conversion of $CS_2$ in less than 5 minutes. From these examples, it appears that increasing amounts of $CS_2$ can be removed from a product stream by using increasing amounts of alkanolamine proportional to the amount of $CS_2$ present in the initial sulfide product stream. Moreover, $CS_2$ conversion occurs very quickly when an adequate amount of alkanolamine is present in the product mixture, either at room temperature or at elevated temperatures.

Examples 8-10 demonstrate that diluting the alkanolamine does not adversely affect the conversion of $CS_2$ after 30 minutes, and similar conversion rates and speeds are observed. Surprisingly, for Examples 9-10, the $CS_2$ level dropped to zero after only 5 minutes. Examples 11-12 examine the effect of other alkanolamines in converting the $CS_2$ to higher boiling point products after 30 minutes. As is shown in Table III, 1-amino-2-propanol and diethanolamine were effective in converting the $CS_2$, at alkanolamine:$CS_2$ ratios similar to those used for ethanolamine in Examples 1-10.

Examples 13-20

Examples 13-20 were performed as bench scale purifications of a dimethyl sulfide product stream comprising $CS_2$ to demonstrate that the conversion of $CS_2$ in the contacting step could effectively prevent any amount of $CS_2$ from being transferred to the overhead (O/H) purified product stream. Examples 13-20 also examine alternate alkanolamines that can be used during the contacting step. Results are summarized in Table IV. A 500-mL jacketed distillation kettle was equipped with an 8-inch distillation column packed with structured metal packing. To this was attached a condenser and overhead sample collection flask. The kettle was heated using glycol heated to 45° C. and a reflux ratio of 5:5 was used. The exact amount of $CS_2$ present initially in the dimethyl sulfide product stream was not analyzed, but was in the 2000-3000 ppm range.

Surprisingly, alkanolamines that are not β-hydroxy amines were successful in completely converting the $CS_2$ to higher boiling point products. Without being bound by theory, these alternate β-hydroxy amines also may form alternate higher boiling point products by reaction with $CS_2$, which are easily separated from a target sulfide compound (dimethyl sulfide) during distillation. Moreover, in each of Examples 13-20 where the conversion of $CS_2$ during the contacting step was complete, no amount of $CS_2$ (0 ppm) was observed in the purified dimethyl sulfide stream. Example 13 demonstrated that ethanolamine was particularly effective, requiring a loading of 0.5 wt. % (based on the weight of the initial dimethyl sulfide product stream) to convert all of the $CS_2$ present in the dimethyl sulfide stream. Other alkanolamines also were shown to be effective in the conversion of $CS_2$ to higher boiling point products, which can then be easily separated from dimethyl sulfide by conventional distillation.

TABLE I

| | Column T-2 | | | | | | | | | | |
|---|---|---|---|---|---|---|---|---|---|---|---|
| Entry | Kettle $H_2O$, ppm | Kettle $CS_2$, ppm | Overhead $H_2O$, ppm | Overhead $CS_2$, ppm | Product stream, gpm | Product stream ° C. | Reflux, gpm | Pressure, psig | Reboiler steam, lb/hr | Column Temperature (bottom, ° C.) | Column Temperature (top, ° C.) |
| A1 | 181 | 1708 | 243 | 1764 | 3.5 | 62 | 13 | 14 | 1100 | 66 | 67 |
| A2 | 33 | 1669 | 36 | 1901 | 2.5 | 56 | 13 | 9 | 1100 | 60 | 60 |
| A3 | 33 | 1547 | 37 | 1625 | 2.4 | 54 | 13 | 8 | 1100 | 59 | 58 |
| A4 | 21 | 782 | 38 | 1295 | 1.0 | 50 | 14 | 6 | 1100 | 57 | 56 |
| A5 | 41 | 713 | 39 | 1179 | 1.0 | 49 | 14 | 5 | 1100 | 56 | 54 |
| A6 | 29 | 606 | 53 | 970 | 1.0 | 52 | 15 | 6 | 1100 | 57 | 57 |
| A7 | 28 | 507 | 40 | 969 | 1.0 | 50 | 14 | 6 | 1100 | 57 | 56 |
| A8 | 26 | 577 | 45 | 1079 | 1.0 | 49 | 14 | 5 | 1100 | 56 | 54 |
| A9 | 40 | 647 | 38 | 1118 | 1.0 | 49 | 14 | 5 | 1100 | 56 | 55 |

TABLE I-continued

Column T-2

| Entry | Kettle H$_2$O, ppm | Kettle CS$_2$, ppm | Overhead H$_2$O, ppm | Overhead CS$_2$, ppm | Product stream, gpm | Product stream, ° C. | Reflux, gpm | Pressure, psig | Reboiler steam, lb/hr | Column Temperature (bottom, ° C.) | Column Temperature (top, ° C.) |
|---|---|---|---|---|---|---|---|---|---|---|---|
| A10 | 38 | 581 | 51 | 1052 | 1.0 | 51 | 14 | 6 | 1100 | 57 | 56 |
| A11 | 51 | 572 | 46 | 1128 | 1.0 | 51 | 14 | 5 | 1100 | 57 | 57 |
| A12 | 61 | 591 | 50 | 1106 | 1.0 | 49 | 14 | 5 | 1100 | 55 | 54 |
| A13 | 24 | 605 | 38 | 1118 | 1.0 | 49 | 14 | 6 | 1100 | 55 | 54 |
| A14 | 35 | 581 | 37 | 1115 | 1.0 | 51 | 16 | 6 | 1245 | 57 | 57 |
| A15 | 55 | 724 | 63 | 1019 | 1.0 | 53 | 18 | 7 | 1445 | 59 | 58 |
| A16 | 32 | 699 | 39 | 936 | 1.0 | 57 | 19 | 6 | 1440 | 64 | 59 |
| A17 | 25 | 744 | 39 | 1015 | 1.0 | 57 | 18 | 6 | 1408 | 63 | 59 |
| A18 | 54 | 739 | 50 | 1009 | 1.0 | 54 | 19 | 7 | 1407 | 61 | 58 |
| A19 | 53 | 720 | 60 | 1007 | 1.0 | 56 | 19 | 6 | 1411 | 63 | 59 |
| A20 | 56 | 705 | 52 | 1046 | 1.0 | 56 | 19 | 7 | 1425 | 62 | 59 |
| A21 | 46 | 695 | 49 | 976 | 1.0 | 56 | 19 | 7 | 1425 | 63 | 59 |
| A22 | 35 | 916 | 57 | 795 | 1.0 | 59 | 14 | 39 | 1350 | 65 | 60 |
| A23 | 31 | 1359 | 65 | 584 | 1.0 | 81 | 16 | 34 | 1350 | 87 | 88 |
| A24 | 38 | 1524 | 45 | 615 | 1.0 | 78 | 14 | 41 | 1350 | 84 | 85 |
| A25 | 58 | 1747 | 44 | 635 | 1.0 | 82 | 15 | 39 | 1350 | 96 | 90 |
| A26 | 25 | 1640 | 721 | 362 | 1.0 | 81 | 15 | 37 | 1350 | 95 | 89 |
| A27 | 120 | 1295 | 110 | 546 | 1.0 | 80 | 15 | 36 | 1350 | 94 | 88 |
| A28 | 41 | 1787 | 84 | 532 | 1.0 | 79 | 14 | 51 | 1350 | 93 | 87 |
| A29 | 64 | 1715 | 85 | 548 | 1.0 | 89 | 14 | 49 | 1350 | 103 | 97 |
| A30 | 40 | 1913 | 77 | 619 | 1.0 | 88 | 14 | 49 | 1350 | 102 | 96 |
| A31 | 50 | 2130 | 83 | 701 | 1.0 | 88 | 14 | 50 | 1350 | 101 | 96 |
| A32 | 232 | 1434 | 170 | 559 | 1.0 | 88 | 15 | 48 | 1350 | 101 | 96 |
| A33 | 47 | 2008 | 87 | 615 | 1.0 | 88 | 15 | 48 | 1350 | 102 | 95 |
| A34 | 73 | 2154 | 73 | 661 | 1.0 | 87 | 14 | 49 | 1350 | 101 | 95 |
| A35 | 166 | 1520 | 253 | 444 | 1.0 | 88 | 15 | 49 | 1350 | 101 | 96 |
| A36 | 292 | 1649 | 344 | 633 | 1.0 | 88 | 15 | 49 | 1350 | 102 | 96 |
| A37 | 66 | 2259 | 45 | 601 | 1.0 | 88 | 14 | 48 | 1350 | 102 | 96 |
| A38 | 116 | 2427 | 84 | 724 | 1.0 | 87 | 14 | 49 | 1350 | 101 | 95 |
| A39 | 40 | 1599 | 90 | 786 | 1.0 | 87 | 3 | 61 | 340 | 101 | 95 |
| A40 | 60 | 1344 | 75 | 765 | 1.0 | 94 | 2 | 63 | 478 | 108 | 103 |
| A41 | 60 | 1474 | 86 | 845 | 1.0 | 94 | 6 | 52 | 686 | 108 | 102 |
| A42 | 29 | 2052 | 84 | 943 | 1.0 | 89 | 11 | 52 | 1051 | 103 | 97 |
| A43 | 65 | 2247 | 52 | 825 | 1.0 | 89 | 12 | 52 | 1195 | 103 | 97 |
| A44 | 56 | 2434 | 53 | 829 | 1.0 | 89 | 14 | 52 | 1309 | 103 | 97 |

TABLE II

Column T-3.

| Entry | Kettle H$_2$O, ppm | Kettle CS$_2$, ppm | Overhead H$_2$O, ppm | Overhead CS$_2$, ppm | Product stream, gpm | Product stream, ° C. | Reflux, gpm | Pressure, psig | Reboiler steam, lb/hr | Column Temperature (bottom, ° C.) | Column Temperature (top, ° C.) |
|---|---|---|---|---|---|---|---|---|---|---|---|
| B1 | 32 | 5934 | 94 | 2020 | 4 | 81 | 35 | 53 | 3000+ | 101 | 99 |
| B2 | 45 | 5792 | 27 | 1847 | 4 | 82 | 45 | 58 | 3000+ | 105 | 104 |
| B3 | 33 | 5507 | 53 | 1585 | 4 | 79 | 46 | 60 | 3000+ | 105 | 104 |
| B4 | 24 | 4425 | 37 | 1209 | 4 | 78 | 50 | 63 | 3000+ | 108 | 107 |
| B5 | 42 | 4321 | 40 | 971 | 4 | 74 | 51 | 65 | 3000+ | 108 | 107 |
| B6 | 810 | 4250 | 22 | 902 | 4 | 76 | 50 | 66 | 3000+ | 109 | 108 |
| B7 | 30 | 4092 | 28 | 868 | 4 | 79 | 49 | 63 | 3000+ | 107 | 107 |
| B8 | 33 | 4100 | 52 | 955 | 4 | 78 | 47 | 59 | 3000+ | 105 | 104 |
| B9 | 37 | 4155 | 37 | 1032 | 4 | 79 | 48 | 61 | 3000+ | 106 | 106 |
| B10 | 22 | 4337 | 26 | 874 | 4 | 83 | 50 | 66 | 3000+ | 108 | 108 |
| B11 | 0 | 2955 | 0 | 870 | 4 | 79 | 49 | 64 | 3000+ | 108 | 107 |
| B12 | 76 | 4042 | 32 | 1001 | 4 | 77 | 48 | 59 | 3000+ | 104 | 104 |
| B13 | 23 | 4144 | 41 | 967 | 4 | 77 | 48 | 59 | 3000+ | 104 | 104 |
| B14 | 11 | 4062 | 25 | 1016 | 4 | 78 | 49 | 63 | 3000+ | 107 | 107 |
| B15 | 46 | 4108 | 29 | 954 | 4 | 79 | 49 | 63 | 3000+ | 107 | 107 |
| B16 | 72 | 4307 | 52 | 1048 | 4 | 77 | 47 | 61 | 3000+ | 106 | 105 |
| B17 | 38 | 4201 | 43 | 1037 | 4 | 77 | 48 | 62 | 3000+ | 106 | 106 |
| B18 | 20 | 4161 | 38 | 1016 | 4 | 77 | 48 | 60 | 3000+ | 105 | 104 |
| B19 | 42 | 4437 | 38 | 937 | 3 | 86 | 49 | 63 | 3000+ | 107 | 107 |
| B20 | 35 | 4531 | 49 | 924 | 3 | 84 | 49 | 63 | 3000+ | 107 | 106 |
| B21 | 55 | 4499 | 47 | 905 | 4 | 83 | 50 | 63 | 3000+ | 107 | 106 |

TABLE II-continued

Column T-3.

| Entry | Kettle H₂O, ppm | Kettle CS₂, ppm | Overhead H₂O, ppm | Overhead CS₂, ppm | Product stream, gpm | Product stream, °C. | Reflux, gpm | Pressure, psig | Reboiler steam, lb/hr | Column Temperature (bottom, °C.) | Column Temperature (top, °C.) |
|---|---|---|---|---|---|---|---|---|---|---|---|
| B22 | 35  | 4344 | 39  | 952  | 4 | 78 | 50 | 65 | 3000+ | 108 | 107 |
| B23 | 30  | 4106 | 41  | 1002 | 4 | 78 | 50 | 65 | 3000+ | 108 | 108 |
| B24 | 35  | 4060 | 51  | 889  | 4 | 78 | 50 | 65 | 3000+ | 108 | 225 |
| B25 | 35  | 4096 | 46  | 990  | 4 | 77 | 48 | 61 | 3000+ | 106 | 221 |
| B26 | 32  | 4082 | 104 | 819  | 4 | 78 | 48 | 66 | 3000+ | 109 | 226 |
| B27 | 188 | 3337 | 443 | 432  | 4 | 79 | 49 | 69 | 3000+ | 110 | 229 |
| B28 | 23  | 3927 | 93  | 799  | 4 | 78 | 48 | 67 | 3000+ | 109 | 228 |
| B29 | 37  | 4310 | 68  | 820  | 4 | 36 | 48 | 65 | 3000+ | 108 | 224 |
| B30 | 41  | 4003 | 124 | 656  | 4 | 39 | 43 | 63 | 3000+ | 107 | 224 |
| B31 | 99  | 3913 | 76  | 972  | 4 | 29 | 40 | 60 | 3000+ | 105 | 219 |
| B32 | 48  | 3797 | 882 | 754  | 4 | 40 | 42 | 66 | 3000+ | 108 | 225 |
| B33 | 56  | 3836 | 643 | 1029 | 4 | 42 | 41 | 65 | 3000+ | 108 | 225 |
| B34 | 49  | 4027 | 105 | 896  | 4 | 37 | 40 | 63 | 3000+ | 107 | 223 |
| B35 | 73  | 4002 | 61  | 1108 | 4 | 31 | 38 | 61 | 3000+ | 106 | 221 |
| B36 | 83  | 3688 | 771 | 750  | 4 | 42 | 39 | 66 | 3000+ | 108 | 226 |
| B37 | 166 | 3015 | 226 | 725  | 4 | 42 | 39 | 66 | 3000+ | 108 | 226 |
| B38 | 90  | 3866 | 273 | 976  | 4 | 31 | 36 | 61 | 3000+ | 105 | 220 |
| B39 | 90  | 3772 | 76  | 1069 | 4 | 31 | 35 | 55 | 3000+ | 102 | 215 |
| B40 | 26  | 3885 | 44  | 1099 | 4 | 36 | 36 | 56 | 3000+ | 103 | 216 |
| B41 | 64  | 3995 | 73  | 1270 | 4 | 32 | 36 | 54 | 3000+ | 102 | 213 |
| B42 | 50  | 3860 | 44  | 1221 | 4 | 30 | 35 | 52 | 3000+ | 101 | 211 |
| B43 | 30  | 3790 | 48  | 1242 | 4 | 34 | 36 | 57 | 3000+ | 103 | 217 |
| B44 | 57  | 4032 | 49  | 1205 | 4 | 38 | 38 | 63 | 3000+ | 107 | 223 |
| B45 | 60  | 4025 | 55  | 1135 | 4 | 31 | 38 | 61 | 3000+ | 106 | 221 |

TABLE III

Examples 1-12.

| Example | Temperature (°C.) | DMS (g) | Alkanolamine (AA) | AA (wt. %) | AA (mmol) | Initial CS₂ (ppmw) | Final CS₂ (ppmw) | AA:CS₂ |
|---|---|---|---|---|---|---|---|---|
| 1 | 20 | 50 | ethanolamine | 0.30 | 2.46 | 2088 | 687 | 1.8 |
| 2 | 20 | 202 | ethanolamine | 0.50 | 16.37 | 2057 | 97 | 3.0 |
| 3 | 36 | — | ethanolamine | 0.70 | — | 2321 | 0 | — |
| 4 | 36 | — | ethanolamine | 0.30 | — | 2046 | 847 | — |
| 5 | 36 | 92 | ethanolamine | 0.50 | 7.53 | 2353 | 375 | 2.6 |
| 6 | 36 | 99 | ethanolamine | 0.71 | 11.46 | 2664 | 46 | 3.3 |
| 7 | 36 | 130 | ethanolamine | 0.85 | 18.01 | 2664 | 0 | 4.0 |
| 8 | 20 | 100 | ethanolamine (85% in methanol) | 0.51 | 8.22 | 2204 | 41 | 2.9 |
| 9 | 20 | 100 | ethanolamine (85% in methanol) | 0.77 | 12.13 | 2363 | 0 | 4.0 |
| 10 | 20 | 100 | ethanolamine (50% in methanol) | 0.70 | 10.92 | 2204 | 0 | 3.9 |
| 11 | 36 | 153 | 1-amino-2-propanol | 0.80 | 11.60 | 2664 | 134 | 2.3 |
| 12 | 36 | 73 | diethanolamine | 0.55 | 5.33 | 2235 | 942 | 2.6 |

TABLE IV

Examples 13-20.

| Example | Chemical name | Alkanolamine Loading (wt %) | Initial CS₂ (ppm) | ppm CS₂ kettle | ppm CS₂ O/H |
|---|---|---|---|---|---|
| 13 | monoethanolamine | 0.5 | 2000-3000 | 0 | 0 |
| 14 | diisopropanolamine | 0.7 | 2000-3000 | 292 | 820 |
| 15 | 3-amino-1-propanol | 0.5 | 2000-3000 | 0 | 0 |
| 16 | 1-amino-2-propanol | 0.5 | 2000-3000 | 0 | 0 |
| 17 | 2-(2-aminoethoxy)ethanol | 0.6 | 2000-3000 | 0 | 0 |
| 18 | 1-amino-2-butanol | 0.6 | 2000-3000 | 304 | 0 |
| 19 | ethylene diamine | 0.5 | 2000-3000 | 0 | 0 |
| 20 | methyldiethanolamine | 1.0 | 2000-3000 | 2319 | 3016 |

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following (aspects typically are described as "comprising" but, alternatively, can "consist essentially of" or "consist of" unless specifically stated otherwise):

Aspect 1. A process to purify a product stream containing a sulfide compound and $CS_2$, the process comprising:

(i) contacting the product stream with an alkanolamine to convert at least a portion of the $CS_2$ to a higher boiling point product; and (ii) removing at least a portion of the higher boiling point product from the product stream to form a purified sulfide stream.

Aspect 2. The process defined in aspect 1, wherein the sulfide compound has formula (I):

wherein:

$R^1$ and $R^2$ independently are a $C_1$ to Cis substituted or unsubstituted, cycloalkyl group or linear or branched alkyl group.

Aspect 3. The process defined in aspect 2, wherein $R^1$ and $R^2$ independently are a branched alkyl group.

Aspect 4. The process defined in aspect 2, wherein $R^1$ and $R^2$ independently are a linear alkyl group.

Aspect 5. The process defined in aspect 2, wherein $R^1$ and $R^2$ independently are a substituted alkyl group (e.g., a phenyl-substituted alkyl group).

Aspect 6. The process defined in any one of aspects 2-5, wherein $R^1$ and $R^2$ independently are a $C_1$ to Cie alkyl group.

Aspect 7. The process defined in aspect 2, wherein $R^1$ and $R^2$ independently are a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group.

Aspect 8. The process defined in aspect 2, wherein $R^1$ and $R^2$ independently are a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, or a tert-amyl group.

Aspect 9. The process defined in aspect 2, wherein $R^1$ and $R^2$ independently are a methyl group or an ethyl group.

Aspect 10. The process defined in any one of aspects 2-9, wherein $R^1$ and $R^2$ are different.

Aspect 11. The process defined in any one of aspects 2-9, wherein $R^1$ and $R^2$ are the same.

Aspect 12. The process defined in aspect 1 or 2, wherein the sulfide compound is methyl ethyl sulfide, methyl isopropyl sulfide, methyl dodecyl sulfide, ethyl octyl sulfide, n-pentyl n-heptyl sulfide, or any combination thereof.

Aspect 13. The process defined in aspect 1 or 2, wherein the sulfide compound is methyl ethyl sulfide.

Aspect 14. The process defined in aspect 1 or 2, wherein the sulfide compound is dimethyl sulfide, diethyl sulfide, di-n-propyl sulfide, di-iso-propyl sulfide, di-n-butyl sulfide, di-n-pentyl sulfide, di-n-hexyl sulfide, di-n-heptyl sulfide, di-n-octyl sulfide, di-n-dodecyl sulfide, or any combination thereof.

Aspect 15. The process defined in aspect 1 or 2, wherein the sulfide compound is dimethyl sulfide.

Aspect 16. The process defined in any one of aspects 1-15, wherein the sulfide compound is a liquid at any set of conditions disclosed herein (e.g., standard temperature and pressure, 0° C. and 2 atm, or −10° C. and 2 atm).

Aspect 17. The process defined in any one of aspects 1-16, wherein the product stream comprises any wt. % of the sulfide compound disclosed herein, e.g., at least about 95 wt. %, at least about 99 wt. %, from about 95 wt. % to about 99.99 wt. %, or from about 99 wt. % to about 99.9 wt. %.

Aspect 18. The process defined in any one of aspects 1-17, wherein the product stream comprises any minimum amount of $CS_2$ disclosed herein, e.g., a minimum of about 250 ppm, a minimum of about 500 ppm, or a minimum of about 1000 ppm (by weight).

Aspect 19. The process defined in any one of aspects 1-18, wherein the product stream comprises an amount of $CS_2$ in any range disclosed herein, e.g., from about 250 to about 5000 ppm, from about 500 ppm to about 10,000 ppm, from about 1000 to 5000 ppm, or from about 2000 to about 4000 ppm (by weight).

Aspect 20. The process defined in any one of aspects 1-19, wherein the product stream further comprises an amount of $H_2S$ in any range disclosed herein, e.g., from about 1 to about 100 ppm, from about 100 ppm to about 250 ppm, or from about 250 ppm to about 1000 ppm (by weight).

Aspect 21. The process defined in any one of aspects 1-20, wherein the alkanolamine is a $C_1$ to $C_{12}$ alkanolamine, or a $C_2$ to $C_6$ alkanolamine.

Aspect 22. The process defined in any one of aspects 1-21, wherein the alkanolamine is a monoalkanolamine (e.g., methanolamine, ethanolamine, n-propanolamine, isopropanolamine, n-butanolamine, isobutanolamine, or any combination thereof); alternatively, a dialkanolamine (e.g., diethanolamine, diisopropanolamine, or a combination thereof); or alternatively, a trialkanolamine (e.g., triethanolamine).

Aspect 23. The process defined in any one of aspects 1-22, wherein the alkanolamine contains a primary amine; alternatively, a secondary amine; or alternatively, a tertiary amine.

Aspect 24. The process defined in any one of aspects 1-23, wherein the alkanolamine comprises a heteroatom-containing linking group between the hydroxy and the amine group.

Aspect 25. The process defined in any one of aspects 1-21, wherein the alkanolamine is al-hydroxy amine having the formula (II):

wherein $R^3$, $R^4$, $R^5$, and $R^6$ independently are H or a $C_1$ to $C_{12}$ alkyl group.

Aspect 26. The process defined in any one of aspects 1-25, wherein the alkanolamine is a liquid at standard temperature and pressure (20° C. and 1 atm).

Aspect 27. The process defined in any one of aspects 1-26, wherein the alkanolamine does not react with the sulfide compound.

Aspect 28. The process defined in any one of aspects 1-27, wherein in step (i), the product stream is contacted with the alkanolamine in a diluent.

Aspect 29. The process defined in aspect 28, wherein the diluent comprises a $C_1$ to $C_3$ alcohol.

Aspect 30. The process defined in aspect 28 or 29, wherein a weight ratio of alkanolamine:diluent is in any suitable range or any range disclosed herein, e.g., from about 95:5 to about 25:75, from about 85:15 to about 50:50, or from about 90:10 to about 70:30.

Aspect 31. The process defined in any one of aspects 1-30, wherein step (i) is conducted at a temperature in any suitable range or any range disclosed herein, e.g., from about 15° C. to about 85° C., from about 20° C. to about 70° C., or from about 25° C. to about 60° C.

Aspect 32. The process defined in any one of aspects 1-31, wherein step (i) is conducted at a pressure in any suitable range or any range disclosed herein, e.g., from ambient to about 100 psig (689 kPag), or from about 5 to about 60 psig (34 to 414 kPag).

Aspect 33. The process defined in any one of aspects 1-32, wherein in step (i), a molar ratio of alkanolamine:$CS_2$ is in any suitable range or any range disclosed herein, e.g., from about 1:1 to about 20:1, from about 1.5:1 to about 10:1, or from about 2:1 to about 6:1.

Aspect 34. The process defined in any one of aspects 1-33, wherein in step (i), an amount of the alkanolamine added to the product stream is in any suitable range or any range disclosed herein, e.g., from about 0.1 to about 2 wt. %, from about 0.2 to about 1 wt. %, or from about 0.4 to about 1.5 wt. %, based on the weight of the product stream.

Aspect 35. The process defined in any one of aspects 1-34, wherein step (i) is conducted for a time period in any suitable range or any range disclosed herein, e.g., from about 1 min to about 24 hr, from about 2 min to about 2 hr, from about 2 min to about 30 min, or from about 5 min to about 1 hr.

Aspect 36. The process defined in any one of aspects 1-35, wherein in step (i), contacting the product stream with the alkanolamine comprises agitating a mixture of the product stream and the alkanolamine.

Aspect 37. The process defined in any one of aspects 1-36, wherein in step (i), any percentage amount disclosed herein of the $CS_2$ is converted to the higher boiling point product, e.g., at least about 50 wt. %, at least about 80 wt. %, from about 60 wt. % to about 99.99 wt. %, or from about 90 to about 99.99 wt. %.

Aspect 38. The process defined in any one of aspects 1-37, wherein the higher boiling point product comprises a heterocyclic organic compound, e.g., with oxygen, nitrogen, sulfur, or any combination thereof, in the ring.

Aspect 39. The process defined in any one of aspects 1-38, wherein the higher boiling point product has a boiling point at least 30° C. greater than the boiling point of the sulfide compound.

Aspect 40. The process defined in any one of aspects 1-39, wherein the higher boiling point product is a liquid at standard conditions or any conditions disclosed herein (e.g., standard temperature and pressure, 0° C. at 2 atm, or −10° C. at 2 atm).

Aspect 41. The process defined in any one of aspects 1-40, wherein in step (ii), the higher boiling point product is removed from the product stream using any suitable technique or any technique disclosed herein, e.g., extraction, filtration, evaporation, distillation, or any combination thereof, to form the purified sulfide stream.

Aspect 42. The process defined in any one of aspects 1-41, wherein in step (ii), the higher boiling point product is removed from the product stream using distillation to form the purified sulfide stream.

Aspect 43. The process defined in aspect 42, wherein distillation is performed at any suitable conditions, e.g., a pressure from ambient to about 100 psig and a temperature from about 35° C. to about 125° C.

Aspect 44. The process defined in any one of aspects 1-43, wherein in step (ii), any percentage amount disclosed herein of the higher boiling point product is removed from the product stream, e.g., at least about 50 wt. %, at least about 80 wt. %, from about 60 to about 99.99 wt. %, or from about 90 to about 99.99 wt. %.

Aspect 45. The process defined in any one of aspects 1-44, wherein the purified sulfide stream comprises any wt. % of the sulfide compound disclosed herein, e.g., at least about 99.9 wt. %, at least about 99.99 wt. %, or at least about 99.995 wt. %.

Aspect 46. The process defined in any one of aspects 1-45, wherein the purified sulfide stream comprises an amount of $CS_2$ in any range disclosed herein, e.g. a maximum of about 200 ppm, a maximum of about 100 ppm, a maximum of about 75 ppm, a maximum of about 25 ppm, a maximum of about 10 ppm, a maximum of about 1 ppm, in a range from about 1 to about 100 ppm, or in a range from about 1 to about 50 ppm (by weight).

Aspect 47. The process defined in any one of aspects 1-46, wherein any percentage amount disclosed herein of the $CS_2$ is converted to a higher boiling point product, e.g., at least about 90 wt. %, at least about 95 wt. %, from about 90 to about 99.9 wt. %, or from about 98 to about 99.99 wt. %.

Aspect 48. The process defined in any one of aspects 1-47, wherein prior to step (i), a ratio of a ppm concentration of $CS_2$ present in the product stream to the ppm concentration of $CS_2$ present in the purified sulfide stream is in any range disclosed herein, e.g., at least about 10:1, at least about 25:1, at least about 100:1, or at least about 500:1.

Aspect 49. The process defined in any one of aspects 1-48, further comprising the steps of:

(a) determining a concentration of the $CS_2$ in the product stream; and (b) adjusting an amount of the alkanolamine contacted with the product stream based on the concentration of the $CS_2$ in the product stream.

Aspect 50. The process defined in any one of aspects 1-49, further comprising the steps of:

(A) determining a concentration of the $CS_2$ in the purified sulfide stream; and (B) adjusting an amount of the alkanolamine contacted with the product stream based on the concentration of the $CS_2$ in the purified sulfide stream.

Aspect 51. A mercaptan and sulfide production system comprising (a) a mercaptan synthesis unit configured to produce a reaction mixture containing a mercaptan compound and a sulfide compound from an alcohol feed stream and a $H_2S$ feed stream (e.g., producing methyl mercaptan and dimethyl sulfide from methanol and $H_2S$, or producing ethyl mercaptan and diethyl sulfide from ethanol and $H_2S$, etc.), the mercaptan synthesis unit comprising a fixed bed catalytic flow reactor; (b) a product purification and fractionation unit configured to isolate a mercaptan product stream and a sulfide product stream (comprising the sulfide compound and $CS_2$) from the reaction mixture, the product purification and fractionating unit comprising one or more separators; and (c) a distillation tower configured to separate at least a portion of a higher boiling point product from the sulfide compound in the sulfide product stream to form a purified sulfide stream containing 100 ppm or less $CS_2$ exiting the top of the distillation tower.

Aspect 52. The system defined in aspect 51, wherein the system further comprises (d) a first inlet for introducing the sulfide product stream and a second inlet for introducing an alkanolamine into the distillation tower, wherein the distillation tower is further configured for contacting the alkanolamine with the sulfide product stream to convert at least a portion of the $CS_2$ in the sulfide product stream to the higher boiling point product.

Aspect 53. The system defined in aspect 51, wherein the system further comprises a (d) distillation tower inlet configured to introduce a mixed stream of an alkanolamine and the sulfide product stream into the distillation tower, wherein at least a portion of the $CS_2$ in the sulfide product stream is converted to the higher boiling point product.

Aspect 54. The system defined in any one of aspects 52-53, further comprising (e) an analytical system (e.g., a sulfur chemiluminescence detector) configured to measure a concentration of $CS_2$ in the purified sulfide stream exiting the top of the distillation tower; and (f) a feedback controller configured to adjust an amount of the alkanolamine introduced into the distillation tower based on the concentration of $CS_2$ measured by the analytical system (e.g., the amount of $CS_2$ measured in the purified sulfide stream is compared to a set point concentration of $CS_2$, and when the measured concentration of $CS_2$ is greater than the set point concentration of $CS_2$, more alkanolamine is added).

Aspect 55. The system defined in aspect 54, wherein (e) the analytical system is further configured to measure a concentration of $CS_2$ in the sulfide product stream; and (f) the feedback controller is further configured to maintain a molar feed ratio of alkanolamine:$CS_2$ (molar feed rate of alkanolamine introduced directly into the tower or in the mixed stream introduced into the tower divided by the molar feed rate of $CS_2$ in the sulfide product stream introduced directly into the tower or in the mixed stream introduced into the tower) in any suitable range or any range disclosed herein, e.g., from about 1:1 to about 20:1, from about 1.5:1 to about 10:1, or from about 2:1 to about 6:1.

Aspect 56. The system defined in any one of aspects 52-55, wherein the alkanolamine is defined in any one of aspects 21-27 (e.g., ethanolamine).

Aspect 57. The system defined in any one of aspects 51-56, wherein the sulfide compound is defined in any one of aspects 2-16 (e.g., dimethyl sulfide).

Aspect 58. The system defined in any one of aspects 51-57, wherein the sulfide product stream contains less than 25 ppm mercaptan compounds, or less than 5 ppm mercaptan compounds (or thiol compounds), and less than 500 ppm water, or less than 200 ppm water.

We claim:

1. A mercaptan and sulfide production system comprising:
   (a) a mercaptan synthesis unit configured to produce a reaction mixture containing a mercaptan compound and a sulfide compound from an alcohol feed stream and a $H_2S$ feed stream;
   (b) a product purification and fractionation unit configured to isolate a mercaptan product stream and a sulfide product stream from the reaction mixture, the sulfide product stream comprising the sulfide compound and $CS_2$;
   (c) a distillation tower configured to separate at least a portion of a higher boiling point product from the sulfide compound in the sulfide product stream to form a purified sulfide stream containing 100 ppm or less $CS_2$ exiting a top of the distillation tower; and
   (d)(1) a first inlet for introducing the sulfide product stream and a second inlet for introducing an alkanolamine into the distillation tower, wherein the distillation tower is further configured to contact the alkanolamine with the sulfide product stream to convert at least a portion of the $CS_2$ in the sulfide product stream to the higher boiling point product, or
   (d)(2) a distillation tower inlet configured to introduce a mixed stream of an alkanolamine and the sulfide product stream into the distillation tower, wherein at least a portion of the $CS_2$ in the sulfide product stream is converted to the higher boiling point product.

2. The system of claim 1, wherein:
   the mercaptan synthesis unit comprises a fixed bed catalytic flow reactor;
   the product purification and fractionating unit comprises one or more separators;
   the alcohol feed stream comprises methanol;
   the mercaptan product stream comprises methyl mercaptan;
   the sulfide compound comprises dimethyl sulfide; and
   the alkanolamine comprises ethanolamine.

3. The system of claim 1, further comprising:
   (e) an analytical system configured to measure a concentration of $CS_2$ in the purified sulfide stream exiting the top of the distillation tower; and
   (f) a feedback controller configured to adjust an amount of the alkanolamine introduced into the distillation tower based on the concentration of $CS_2$ measured by the analytical system.

4. The system of claim 3, wherein:
   (e) the analytical system is further configured to measure a concentration of $CS_2$ in the sulfide product stream; and
   (f) the feedback controller is further configured to maintain a molar feed ratio of alkanolamine:$CS_2$ in a range from about 1.5:1 to about 10:1.

5. The system of claim 1, wherein the system comprises (d)(1) the first inlet for introducing the sulfide product stream and the second inlet for introducing the alkanolamine into the distillation tower, wherein the distillation tower is further configured to contact the alkanolamine with the sulfide product stream to convert the at least a portion of the $CS_2$ in the sulfide product stream to the higher boiling point product.

6. The system of claim 5, wherein the mercaptan synthesis unit comprises a fixed bed catalytic flow reactor.

7. The system of claim 5, wherein the product purification and fractionating unit comprises one or more separators.

8. The system of claim 5, wherein the sulfide product stream contains at least about 95 wt. % of the sulfide compound.

9. The system of claim 5, wherein the purified sulfide stream contains:
   at least about 99.9 wt. % of the sulfide compound; and
   less than or equal to about 25 ppm of $CS_2$.

10. The system of claim 5, wherein the sulfide compound is methyl ethyl sulfide or dimethyl sulfide.

11. The system of claim 5, wherein the alkanolamine comprises ethanolamine.

12. The system of claim 5, wherein a ratio of a ppm concentration of $CS_2$ in the sulfide product stream in the product purification and fractionation unit to a ppm concentration of $CS_2$ in the purified sulfide stream exiting the top of the distillation tower is at least about 100:1.

13. The system of claim 1, wherein the system comprises (d)(2) the distillation tower inlet configured to introduce the mixed stream of the alkanolamine and the sulfide product stream into the distillation tower, wherein the at least a portion of the $CS_2$ in the sulfide product stream is converted to the higher boiling point product.

14. The system of claim 13, wherein the mercaptan synthesis unit comprises a fixed bed catalytic flow reactor.

15. The system of claim 13, wherein the product purification and fractionating unit comprises one or more separators.

16. The system of claim 13, wherein the sulfide product stream contains at least about 95 wt. % of the sulfide compound.

17. The system of claim 13, wherein the purified sulfide stream contains:
 at least about 99.9 wt. % of the sulfide compound; and
 less than or equal to about 25 ppm of $CS_2$.

18. The system of claim 13, wherein the sulfide compound is methyl ethyl sulfide or dimethyl sulfide.

19. The system of claim 13, wherein the alkanolamine comprises ethanolamine.

20. The system of claim 13, wherein a ratio of a ppm concentration of $CS_2$ in the sulfide product stream in the product purification and fractionation unit to a ppm concentration of $CS_2$ in the purified sulfide stream exiting the top of the distillation tower is at least about 100:1.

* * * * *